(12) United States Patent
Carron et al.

(10) Patent No.: US 10,458,917 B2
(45) Date of Patent: Oct. 29, 2019

(54) METHOD OF MEASURING RAMAN SCATTERING AND RELATED SPECTROMETERS AND LASER SOURCES

(71) Applicant: MKS Technology, Inc., Laramie, WY (US)

(72) Inventors: Keith T. Carron, Centennial, WY (US); Celestin P. Zemtsop, Laramie, WY (US); Shane A. Buller, Laramie, WY (US); Scott L. Rudder, Hopewell, NJ (US); Harald R. Guenther, Monmouth Junction, NJ (US)

(73) Assignee: MKS Technology, Inc., Laramie, WY (US)

( * ) Notice: Subject to any disclaimer, the term of this patent is extended or adjusted under 35 U.S.C. 154(b) by 0 days.

(21) Appl. No.: 15/864,340

(22) Filed: Jan. 8, 2018

(65) Prior Publication Data

US 2018/0195965 A1 Jul. 12, 2018

Related U.S. Application Data

(60) Provisional application No. 62/461,493, filed on Feb. 21, 2017, provisional application No. 62/444,026, filed on Jan. 9, 2017.

(51) Int. Cl.
*G01N 21/65* (2006.01)
(52) U.S. Cl.
CPC ..... *G01N 21/65* (2013.01); *G01N 2201/0683* (2013.01); *G01N 2201/06113* (2013.01)

(58) Field of Classification Search
CPC ......... G01N 21/65; G01N 2201/06113; G01N 2201/0683
See application file for complete search history.

(56) References Cited

U.S. PATENT DOCUMENTS

| | | | |
|---|---|---|---|
| 5,151,589 A * | 9/1992 | Takeuchi | B82Y 20/00 250/214 LS |
| 5,473,465 A | 12/1995 | Ye | |
| 5,673,109 A | 9/1997 | Keilbach | |

(Continued)

OTHER PUBLICATIONS

International Search Report for International Application No. PCT/US2018/012755 dated Apr. 30, 2018, 8 pages.

(Continued)

*Primary Examiner* — Hina F Ayub
(74) *Attorney, Agent, or Firm* — TraskBritt

(57) ABSTRACT

A method of measuring Raman scattering includes exciting Raman scattering of a sample with a first wavelength and a second wavelength of electromagnetic radiation traveling along a common optical path to form a first scattered radiation and a second scattered radiation. The first wavelength reaches the sample polarized in a first direction, and the second wavelength reaches the sample polarized in a second direction perpendicular to the first direction. The method includes collecting a first Raman spectrum from the first scattered radiation, collecting a second Raman spectrum from the second scattered radiation, and forming a decomposed Raman spectrum based on the first Raman spectrum and the second Raman spectrum. The decomposed Raman spectrum may be substantially free of noise, such as fluorescence and background radiation. Related spectrometers and laser devices are disclosed.

22 Claims, 12 Drawing Sheets

(56) References Cited

U.S. PATENT DOCUMENTS

| | | | |
|---|---|---|---|
| 5,754,289 A | 5/1998 | Ozaki et al. | |
| 5,795,177 A | 8/1998 | Hirono | |
| 5,841,797 A * | 11/1998 | Ventrudo | G02B 6/02076 372/6 |
| 5,978,125 A * | 11/1999 | Yao | G02F 1/01 359/245 |
| 7,184,142 B2 | 2/2007 | Komachi et al. | |
| 7,403,281 B2 | 7/2008 | Carron et al. | |
| 7,405,822 B2 | 7/2008 | Li et al. | |
| 7,411,670 B2 | 8/2008 | Zribi et al. | |
| 7,423,731 B2 | 9/2008 | Tanitsu et al. | |
| 8,310,671 B1 * | 11/2012 | Nguyen | G01J 3/44 356/301 |
| 8,570,507 B1 | 10/2013 | Cooper et al. | |
| 9,442,072 B2 | 9/2016 | Boyd | |
| 9,581,493 B2 | 2/2017 | Cooper et al. | |
| 2008/0094620 A1 | 4/2008 | Li et al. | |
| 2009/0021724 A1 | 1/2009 | Jahadevan-Jansen et al. | |
| 2009/0212769 A1 | 8/2009 | Stoica et al. | |
| 2012/0069332 A1 | 3/2012 | Frankel | |
| 2013/0162989 A1 | 6/2013 | Chen et al. | |
| 2013/0208272 A1 | 8/2013 | Lettleton | |
| 2014/0268104 A1 | 9/2014 | Tread et al. | |
| 2015/0083922 A1 * | 3/2015 | Graybeal | G01J 3/42 250/343 |
| 2015/0260576 A1 | 9/2015 | Watson et al. | |
| 2016/0103073 A1 * | 4/2016 | Ford | G01N 21/65 356/301 |
| 2017/0370699 A1 * | 12/2017 | Hogan | G01B 9/02059 |
| 2018/0024046 A1 * | 1/2018 | Jessen | G01N 21/1702 73/643 |
| 2018/0164216 A1 * | 6/2018 | Wang | G01J 3/28 |

OTHER PUBLICATIONS

International Written Opinion for International Application No. PCT/US2018/012755 dated Apr. 30, 2018, 8 pages.

* cited by examiner

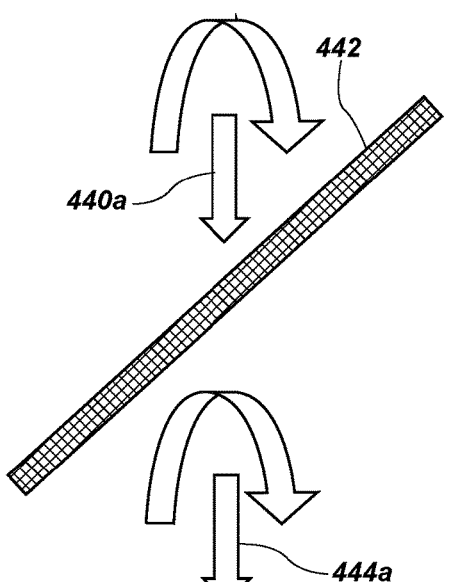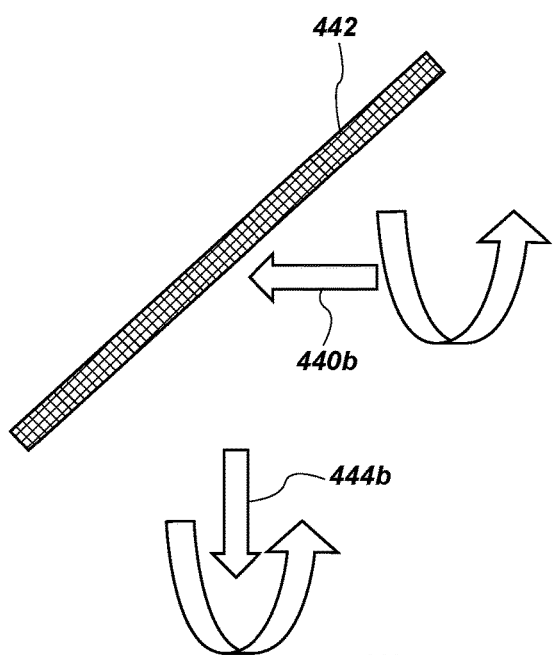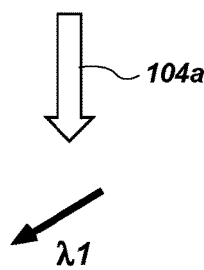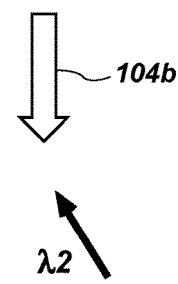
FIG. 5A            FIG. 5B

*Wavenumbers*

*Wavenumbers*

US 10,458,917 B2

METHOD OF MEASURING RAMAN SCATTERING AND RELATED SPECTROMETERS AND LASER SOURCES

CROSS-REFERENCE TO RELATED APPLICATIONS

This application claims the benefit under 35 U.S.C. § 119(e) of U.S. Provisional Patent Application 62/444,026, filed Jan. 9, 2017, and U.S. Provisional Patent Application 62/461,493, filed Feb. 21, 2017, the disclosure of each of which is hereby incorporated herein in its entirety by this reference.

FIELD

Embodiments of the present disclosure relate generally to spectroscopy and to laser sources useful for spectroscopy, such as Raman spectroscopy.

BACKGROUND

Spectroscopy is a general term for the process of measuring energy or intensity as a function of wavelength in a beam of electromagnetic radiation (e.g., light). Many conventional spectrometers include basic features and components such as a slit and a collimator for producing a parallel beam of radiation, one or more prisms or gratings for dispersing radiation through differing angles of deviation based on wavelength, and apparatus for collecting and measuring characteristics of dispersed radiation. Spectroscopy uses absorption, emission, or scattering of electromagnetic radiation by molecules or ions to qualitatively and quantitatively study physical properties and processes of matter.

Light or radiation directed at a target, or sample of physical matter, during operation of a spectrometer system may be referred to as incident radiation. Redirection of incident radiation following contact with a sample commonly is referred to as scattering of radiation. To the extent that atoms or molecules in a sample absorb all or a portion of incident radiation, rather than reflect incident radiation, a sample may become excited, and the energy level of the sample may be increased to a higher energy level. Electromagnetic radiation that passes through a sample may produce a small portion of light that is scattered in a variety of directions. Light that is scattered but continues to have the same wavelength as the incident radiation will also have the same energy, a condition often referred to as Rayleigh or elastically scattered light. Incident radiation that is scattered during a change of vibrational state in molecules may be scattered with a different energy, and such scattered light may be called Raman scattered light. Such phenomena have been used in conjunction with spectroscopy to qualitatively and quantitatively study physical properties and processes, including identification of chemical properties, compositions, and structures of a sample.

A wave of electromagnetic radiation may be characterized by wavelength (the physical length of one complete oscillation) and by frequency of the wave (the number of oscillations per second that pass a given point). The wavelength of incident radiation on a sample may remain substantially unchanged in scattered radiation. Alternatively, the wavelength in scattered radiation may shift to one or more different wavelengths relative to the incident wavelength. The wavelength differential between the incident radiation and the scattered radiation may be referred to as a Raman shift. Spectroscopic measurement of Raman scattered light is a measure of the resulting wavelength of such scattered light.

Raman scattering may occur at wavelengths shifted from the incident light by quanta of molecular vibrations. The phenomenon of Raman scattered light, therefore, is useful in spectroscopy applications for studying qualities and quantities of physical properties and processes, including identification of chemical properties, compositions, and structures in a sample. Measurement of scattered radiation may enable identification of one or more frequencies associated with the sample, as well as the intensities of those shifted frequencies. The frequencies may be used to identify the chemical composition of a sample. If, for example, intensities are plotted on a Y-axis, and frequency or frequencies are plotted on an X-axis, the frequency or frequencies may be expressed as a wavenumber (the reciprocal of the wavelength expressed in centimeters). The X-axis, showing the frequency or frequencies, may be converted to a Raman shift in wavenumbers (a measure of the difference between the observed wavenumber positions of spectral bands) and the wavenumber of radiation appearing in the incident radiation.

Raman scattering offers a significant opportunity for qualitative and quantitative studies of physical properties and processes, including identification of chemical compositions and structure in samples of physical matter. However, Raman scattering is a comparatively weak effect when compared with Rayleigh or elastic scattering. Only about one scattered photon in about $10^6$ to about $10^8$ photons tends to be Raman shifted.

Detection limits in Raman spectroscopy are decreased by ambient light and background interference during sampling. Ambient light usually takes the form of interior lighting or sunlight, which can overpower even the strongest scattering samples. Thus, detectors and samples being scanned are typically fully enclosed to shield from ambient light. Samples that cannot be fully enclosed present special challenges.

Excitation sources used in Raman spectroscopy include gas lasers such as helium-neon, helium-cadmium, argon-ion, krypton-ion, as well as solid-state lasers including Nd-YAG, and diode lasers, solid-state tunable lasers, liquid dye lasers, fiber lasers, and other lasers.

Background interference also comes from non-spontaneous emissions from some types of samples, such as fluorescence. Fluorescence occurs when absorbed radiation is reduced in frequency by internal molecular processes and emitted as radiation that is closer to the red end of the visible light spectrum. Fluorescence sometimes may be strong enough in comparison with the Raman shift to swamp, or substantially overwhelm, the weaker Raman signal. Fluorescence decreases the dynamic range and ultimately the signal-to-noise ratio of data obtained from a sample. Fluorescence can be reduced by exciting at higher wavelengths, such as 1064 nm, but at the cost of expensive components and a loss of signal-to-noise ratios for all samples (i.e., even those samples not plagued by the problem of fluorescence). The loss of signal-to-noise is due to poor detectors at this wavelength and because Raman scattering varies with the wavelength to the negative fourth power ($\lambda^{-4}$).

BRIEF SUMMARY

A method of measuring Raman scattering from a sample includes exciting Raman scattering of a sample with a first wavelength of electromagnetic radiation traveling along an optical path to form a first scattered radiation and exciting Raman scattering of the sample with a second wavelength of electromagnetic radiation traveling along the optical path to form a second scattered radiation. The first wavelength is provided to the sample polarized in a first direction, and the second wavelength is provided to the sample polarized in a second direction perpendicular to the first direction. The method includes collecting a first Raman spectrum from the first scattered radiation, collecting a second Raman spectrum from the second scattered radiation, and forming a decomposed Raman spectrum based on the first Raman spectrum and the second Raman spectrum. The decomposed Raman spectrum may be substantially free of noise, such as fluorescence and background radiation. The first and second Raman spectra need not be collected simultaneously.

In some embodiments, a spectrometer includes a first electromagnetic source adapted to provide a first beam having a first wavelength, a first polarized device configured to convert the first beam to a first polarized beam, a second electromagnetic source adapted to provide a second beam having a second wavelength, a second polarized device configured to convert the second beam to a second polarized beam, a beam combiner configured to combine the first polarized beam and the second polarized beam to form orthogonal collinear polarized beams traveling along a common optical path toward a test sample. Additionally, a detector is configured to receive scattered radiation from the test sample and detect a spectroscopy signal from scattered radiation.

In some embodiments, a laser device includes a first electromagnetic source adapted to provide a first beam having a first wavelength, a second electromagnetic source adapted to provide a second beam having a second wavelength, a first polarized device configured to convert the first beam to a first polarized beam, a second polarized device configured to convert the second beam to a second polarized beam, a beam combiner configured to combine the first polarized beam and the second polarized beam to form orthogonal collinear polarized beams traveling along a common path.

BRIEF DESCRIPTION OF THE DRAWINGS

FIGS. 5A and 5B are simplified diagrams depicting the polarization of laser beams of the laser system depicted in FIG. 4.

DETAILED DESCRIPTION

Figure 1A:
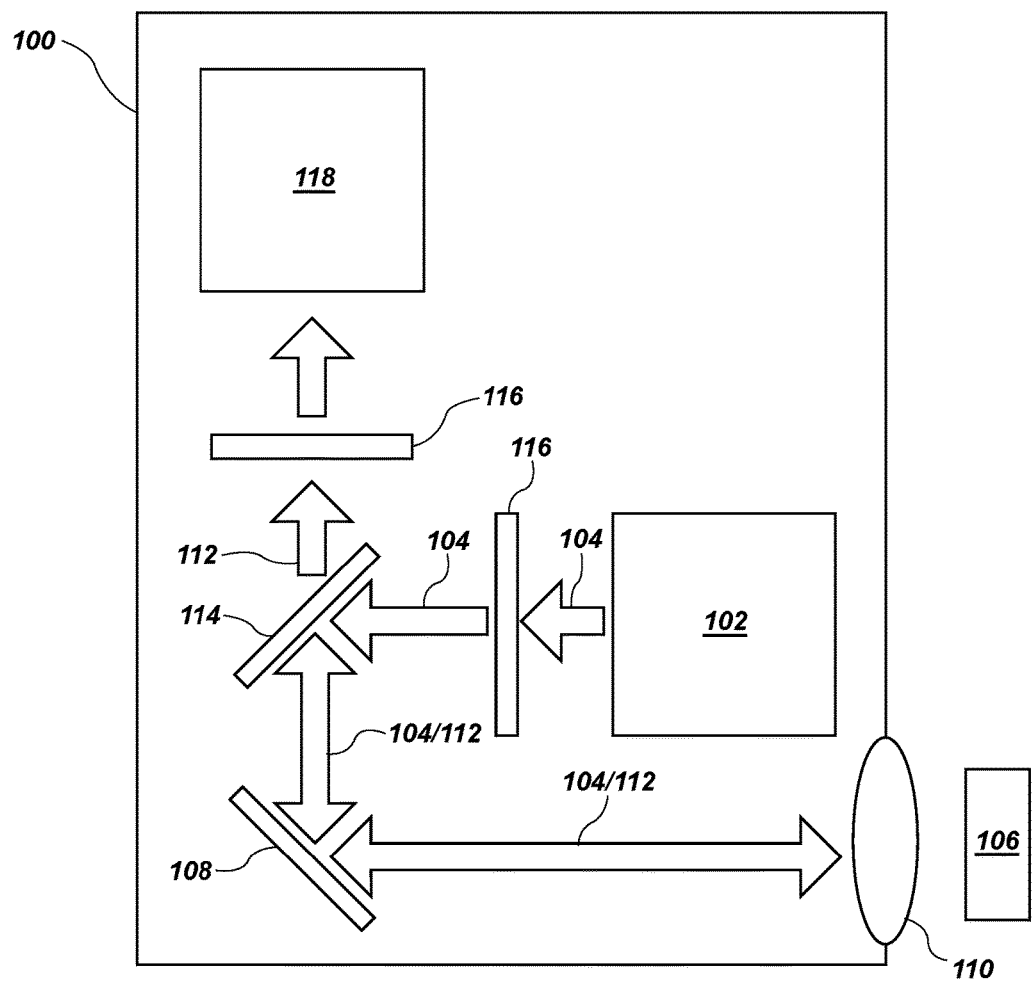
FIG. 1A is a simplified schematic block diagram showing an example embodiment of a spectrometer in accordance with an embodiment of the disclosure.

The illustrations presented herein are not actual views of any particular spectrometer or laser system, but are merely idealized representations that are employed to describe example embodiments of the present disclosure. Additionally, elements common between figures may retain the same numerical designation.

The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, the description provided below does not include all elements to form a complete structure or assembly. Only those process acts and structures necessary to understand the embodiments of the disclosure are described in detail below. Additional conventional acts and structures may be used. Also note, any drawings accompanying the application are for illustrative purposes only, and are thus not drawn to scale. Additionally, elements common between figures may retain the same numerical designation.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter).

Methods and systems described herein may be used to measure two different Raman spectra from the same sample in sequence, without adjusting the operating conditions of the excitation lasers. The excitation lasers may have wavelengths close to one another, such that the measured spectra may be compared and decomposed into a single spectrum substantially free of noise (e.g., background radiation and fluorescence).

FIG. 1A is a simplified schematic block diagram showing an example embodiment of a spectrometer 100. The spectrometer 100 includes a laser system 102. The laser system 102 may provide orthogonal incident plane-polarized beams 104 of radiation to a test sample 106. The incident plane-polarized beams 104 may travel from the laser system 102 to the test sample 106 via one or more mirrors 108 and/or lenses 110. However, in other embodiments, the incident plane-polarized beams 104 may be directed at the test sample 106 without any intervening components in the path of the incident plane-polarized beams 104. The incident plane-polarized beams 104 may also be directed at a holographic transmissive element, a mirror formed with a hole in the mirror, or any other means for directing laser beams. The incident plane-polarized beams 104 travel along a common path toward the test sample 106, but need not exist simultaneously.

The incident plane-polarized beams 104 may be configured to induce or generate, on contact with the test sample 106, scattered radiation 112 having an energy differential different from one or more wavelengths different than the incident plane-polarized beams 104. The scattered radiation 112 may travel back over a portion of the path that the incident plane-polarized beams 104 travel to the test sample 106. A beam splitter 114 may separate the scattered radiation 112 from the incident plane-polarized beams 104, directing the scattered radiation 112 toward a detector 118. As shown in FIG. 1A, the beam splitter 114 may allow the scattered radiation 112, reflecting the incident plane-polarized beams 104. In some embodiments, an optional half-wave plate 116 may be between the beam splitter 114 and the detector 118, or between the laser system 102 and the test sample 106, such as if specular reflectance of the test sample 106 is expected or if the test sample 106 is expected to exhibit a crystalline structure.

Figure 1B:
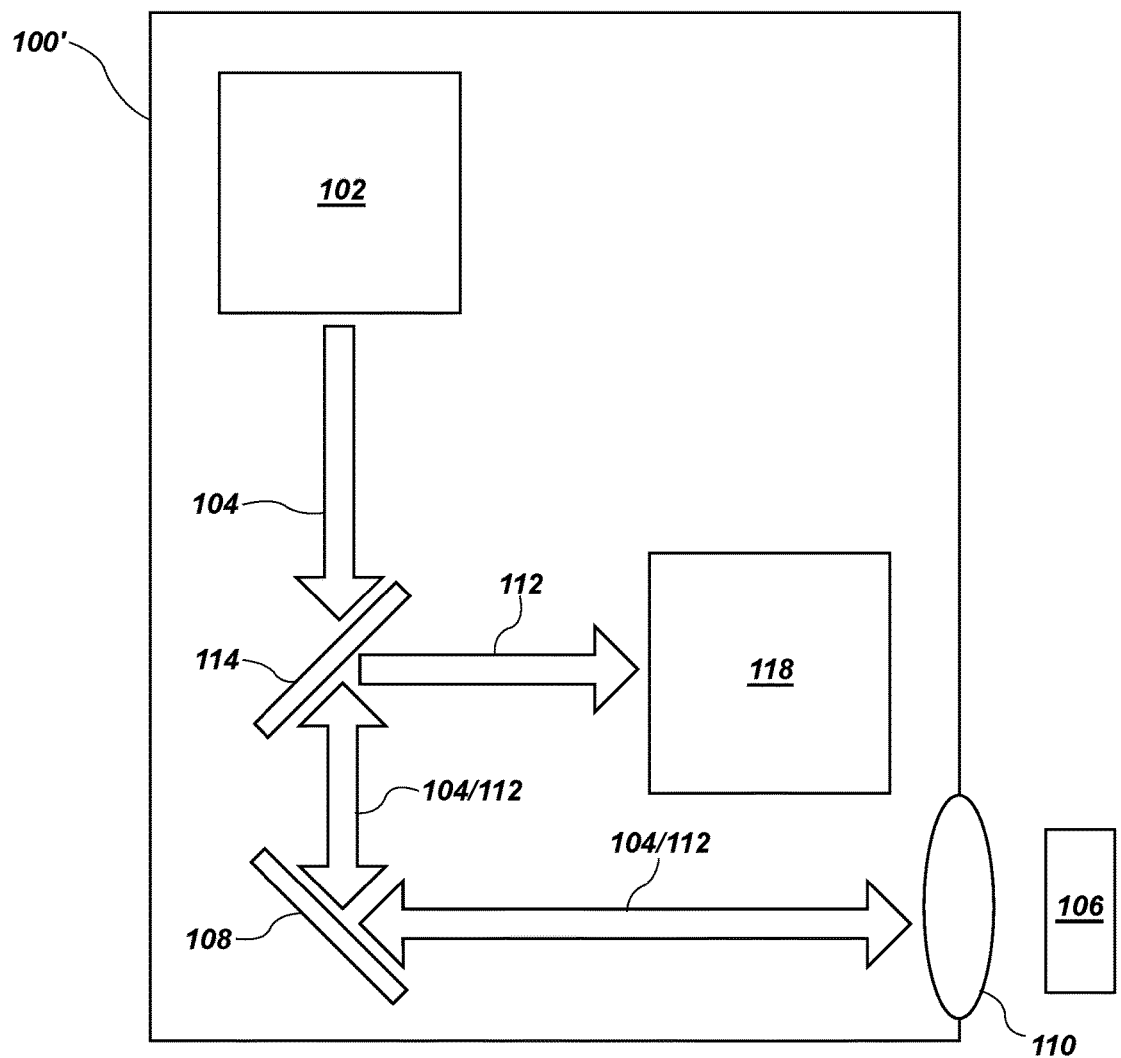
FIG. 1B is a simplified schematic block diagram showing another example embodiment of a spectrometer in accordance with an embodiment of the disclosure.

In some embodiments, and as depicted in FIG. 1B, a spectrometer 100' may include a beam splitter 114 configured to allow the incident plane-polarized beams 104 to pass, and reflect the scattered radiation 112. Thus, the laser system 102 and the detector 118 may be rearranged in the spectrometer 100' from the arrangement depicted in FIG. 1A, based on which beams are reflected and transmitted.

The detector 118 may include a transducer that converts optical energy into an electrical signal. In one embodiment, for example, the detector 118 includes an array of individual transducers that creates an electrical pattern representing the spatially separated wavelengths of the Raman spectrum. A charge-coupled device (CCD) array, for example, may be used as the detector 118. In another embodiment, the detector 118 may include indium-gallium-arsenide (InGaAs) in an active region thereof. Other detectors known in the art may also be used within the spectrometer 100. The spectrometer 100 may optionally include other elements such as a collimated beam tube or a fiber optic waveguide. Detectors and optics are described in U.S. Patent Application Publication 2015/0260576, "Spectrometer," published Sep. 17, 2015; and U.S. Pat. No. 7,403,281, "Raman Spectrometer," issued Jul. 22, 2008; the entire disclosure of each of which is incorporated herein by this reference.

Figure 2:
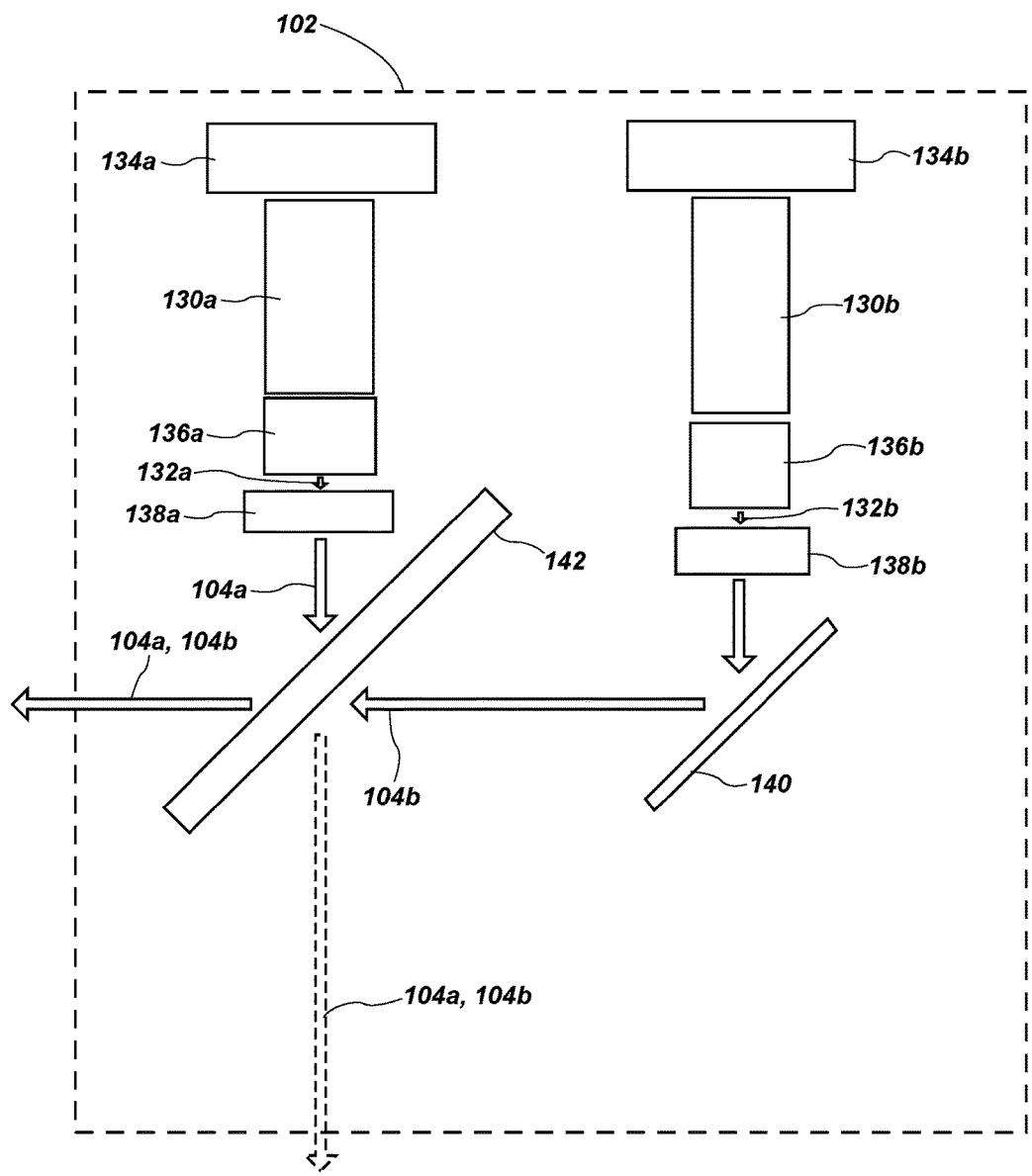
FIG. 2 is a simplified schematic block diagram showing a laser system that forms part of the spectrometer depicted in FIGS. 1A and 1B.

FIG. 2 is a simplified schematic block diagram showing the laser system 102. The laser system 102 may be configured to provide two wavelengths of laser light from different sources along a common optical path. The laser system 102 may include electromagnetic sources 130a, 130b adapted to provide beams 132a, 132b having selected wavelengths. The wavelengths of the beams 132a, 132b may be similar to one another, such as within 20 nm, within 10 nm, within 5 nm, within 2 nm, or even within 0.2 nm. As a non-limiting example, the wavelength of the beam 132a may be 785 nm and the wavelength of the beam 132b may be 783 nm. The electromagnetic sources 130a, 130b may be maintained at constant temperatures or at the same constant temperature by one or more temperature regulators 134a, 134b. For example, the temperature regulators 134a, 134b may be thermoelectric devices or a single thermoelectric device, heat sinks, heat exchangers, etc.

The beams 132a, 132b may each pass through a volume Bragg grating 136a, 136b or other filter configured to reflect wavelengths of radiation outside certain tolerances. For example, the volume Bragg gratings 136a, 136b may be configured to pass electromagnetic radiation within 2 nm of a selected wavelength, within 1 nm of a selected wavelength, within 0.5 nm of a selected wavelength, or even within 0.1 nm of a selected wavelength, and to reflect other wavelengths. Thus, the beams 132a, 132b leaving the volume Bragg gratings 136a, 136b may each be monochromatic.

Figure 3A:
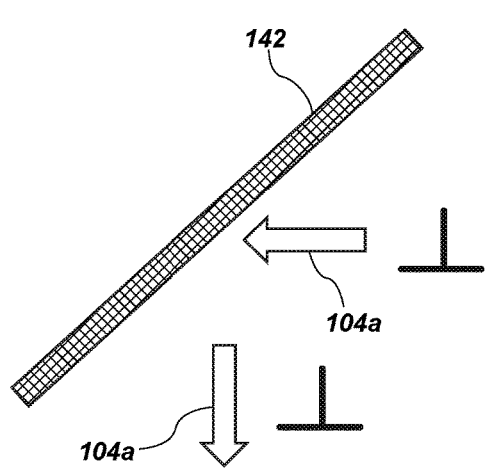
FIGS. 3A and 3B are simplified diagrams depicting the polarization of laser beams of the laser system depicted in FIG. 2.
Figure 3B:
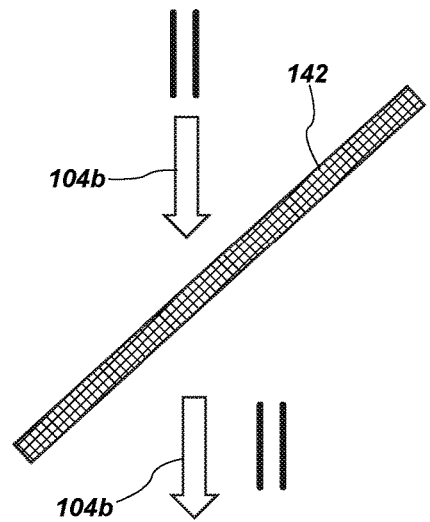

The beams 132a, 132b may pass through linear polarizing devices 138a, 138b configured to convert the beams 132a, 132b to the linear polarized beams 104a, 104b. FIGS. 3A and 3B depict representations of the polarization of the beams 104a, 104b. The linear polarizing devices 138a, 138b (FIG. 2) may be, for example, polarizing filters. The linear polarizing devices 138a, 138b may be configured such that each of the linear polarized beams 104a, 104b are polarized in directions perpendicular to one another in directions of λ1 and λ2, as shown in FIGS. 3A and 3B.

The linear polarized beam 104b may be turned 90° using a turning mirror 140. The linear polarized beams 104a, 104b may pass to a beam combiner 142 configured to combine the first linear polarized beam 104a and the second linear polarized beam 104b, such that the beams 104a, 104b are collinear, traveling along the same path (though the beams 104a, 104b need not travel concurrently along that path). One of the beams 104a, 104b may be transmitted through the beam combiner 142, and the other may be reflected by the beam combiner 142. Thus, the beams 104a, 104b may take either of the paths shown in FIG. 2 (one with a solid arrow, and one with a dashed arrow). One benefit of orienting the beam combiner 142 such that each of the beams 104a, 104b makes a single 90° turn (i.e., the combined beams 104a, 104b shown with a solid arrow in FIG. 2) is that each of the beams 104a, 104b has an independent adjustment plane in the form of the turning mirror 140 (for the beam 104b) or the beam combiner 142 (for the beam 104a). Thus, each of the beams 104a, 104b may be adjusted as necessary to align the beams 104a, 104b with one another and with their target. The beams 104a, 104b may also be adjusted by moving the electromagnetic sources 130a, 130b.

Figure 4:
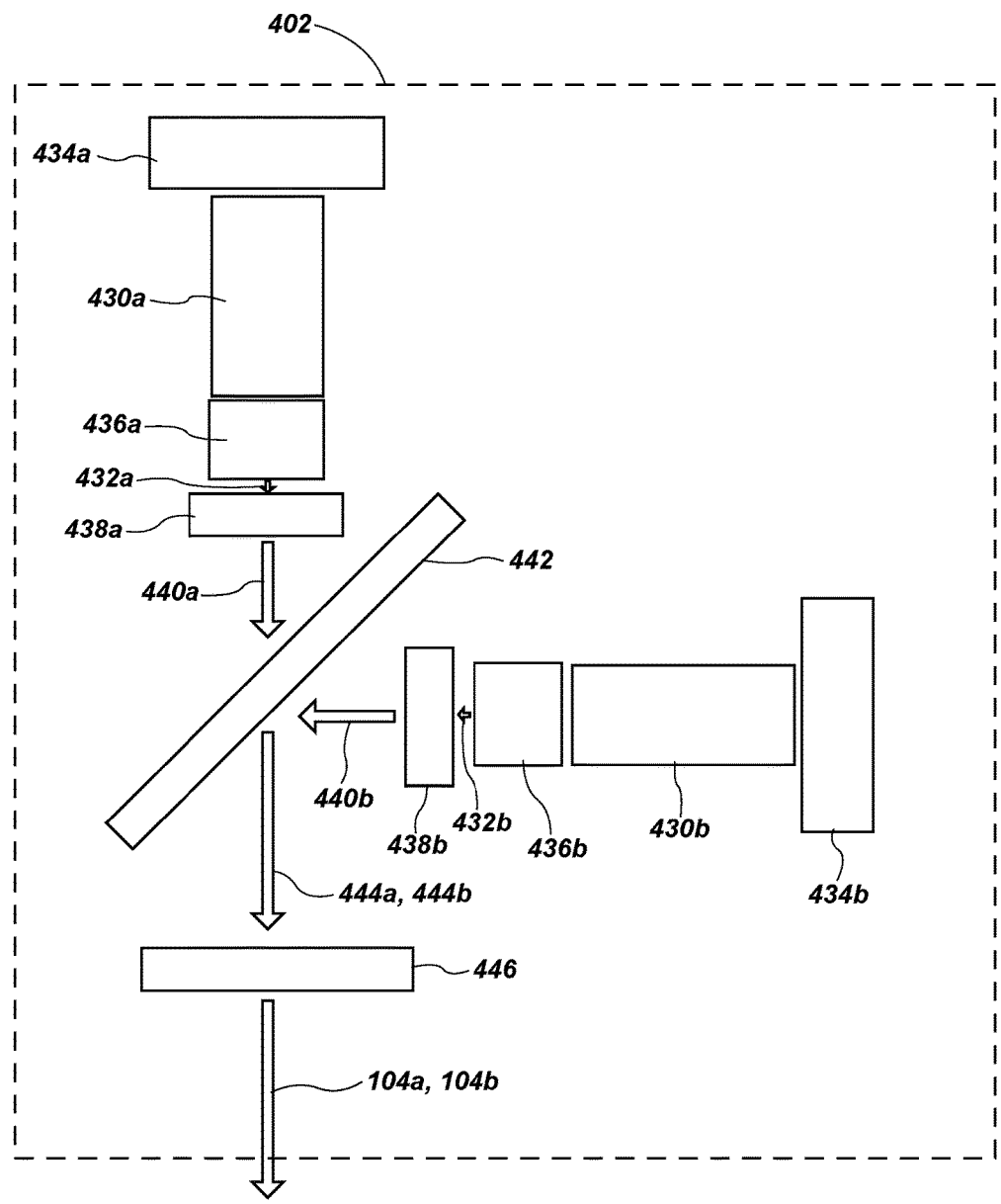
FIG. 4 is a simplified schematic block diagram showing another laser system that may form part of a spectrometer.

FIG. 4 is a simplified schematic block diagram showing another laser system 402 that may be used in a spectrometer 100 (FIG. 1A). For example, the laser system 402 may be used instead of the laser system 102 shown in FIG. 2. The laser system 402 may also be configured to provide two wavelengths of laser light from different sources along a common optical path. The laser system 402 may include electromagnetic sources 430a, 430b adapted to provide beams 432a, 432b having selected wavelengths. The wavelengths of the beams 432a, 432b may be similar to one another, such as within 20 nm, within 10 nm, within 5 nm, within 2 nm, or even within 0.2 nm. In certain embodiments, the difference in wavelengths of the beams 432a, 432b may approach or surpass the resolution limit of the spectrometer 100. For example, the spectrometer 100 may use pixel interpolation to detect wavelength differences of less than 1 wavenumber. As a non-limiting example, the wavelength of the beam 432a may be 785 nm and the wavelength of the beam 432b may be 783 nm. The electromagnetic sources 430a, 430b may be maintained at constant temperatures or at the same constant temperature by one or more temperature regulators 434a, 434b. For example, the temperature regulators 434a, 434b may be thermoelectric devices or a single thermoelectric device, heat sinks, heat exchangers, etc.

The beams 432a, 432b may each pass through a volume Bragg grating 436a, 436b or other filter configured to reflect wavelengths of radiation outside certain tolerances. For example, the volume Bragg gratings 436a, 436b may be configured to pass electromagnetic radiation within 2 nm of a selected wavelength, within 1 nm of a selected wavelength, within 0.5 nm of a selected wavelength, or even within 0.1 nm of a selected wavelength, and to reflect other wavelengths. Thus, the beams 432a, 432b leaving the volume Bragg gratings 436a, 436b may each be monochromatic.

The beams 432a, 432b may pass through circular polarizing devices 438a, 438b configured to convert the beams 432a, 432b to circular polarized beams 440a, 440b. FIGS. 5A and 5B depict representations of the polarization of the circular polarized beams 440a, 440b. The circular polarizing devices 438a, 438b (FIG. 4) may be, for example, quarter-wave plates. The circular polarizing devices 438a, 438b may be configured such that each of the circular polarized beams 440a, 440b are polarized in opposite directions (i.e., the first circular polarized beam 440a may have right circular polarization (FIG. 5A), and the second circular polarized beam 440b may have left circular polarization (FIG. 5B), or vice versa).

The circular polarized beams 440a, 440b may pass to a beam combiner 442 configured to combine the first circular polarized beam 440a and the second circular polarized beam 440b to form collinear circular polarized beams 444a, 444b, polarized in opposite directions (FIGS. 5A and 5B), such that both collinear circular polarized beams 444a, 444b travel along the same path.

A third circular polarizing device 446 may be configured to convert the collinear circular polarized beams 444a, 444b to incident plane-polarized beams 104a, 104b (which together correspond to the incident plane-polarized beams 104 shown in FIG. 1A) directed toward the test sample 106 (see FIG. 1A). Because the circular polarized beams 440a, 440b are polarized in opposite directions, the incident plane-polarized beams 104a, 104b are polarized perpendicular to one another in directions of $\lambda 1$ and $\lambda 2$. The embodiment shown in FIG. 4 does not have include a turning mirror 140 (see FIG. 2) because the electromagnetic sources 430a, 430b may already be oriented such that the circular polarized beams 440a, 440b travel along the same path after the beam combiner 442. The embodiment shown in FIG. 4 may optionally include a turning mirror 140, and the embodiment shown in FIG. 2 may optionally omit the turning mirror 140, as desired for arrangement of the other components. Furthermore, any number of other mirrors or other optical devices may be included in the laser systems 102, 402 as desired, such as to conform the laser systems 102, 402 to a certain size or shape.

Figure 6A:
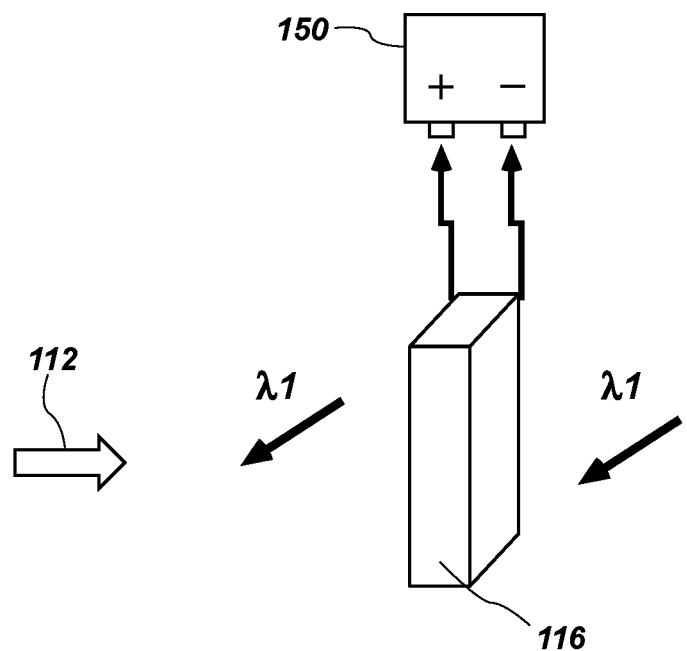
FIGS. 6A and 6B are simplified diagrams depicting how polarized radiation travels within a spectrometer.
Figure 6B:
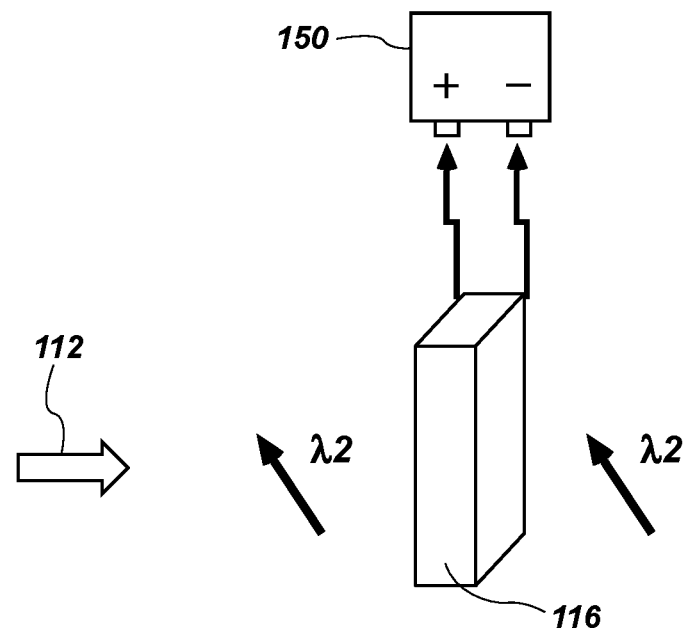

Returning to FIG. 1A, the half-wave plate 116, if present, may receive the scattered radiation 112 from the test sample 106 (e.g., via lenses 110, mirror 108, and beam splitter 114), and may rotate the scattered radiation 112 by 90°. Half-wave plates are described generally in U.S. Pat. No. 5,473,465, "Optical Rotator and Rotation-Angle-Variable Half-Wave-plate Rotator," granted Dec. 5, 1995, the entire disclosure of which is incorporated herein by this reference. The half-wave plate 116 may be, for example, an electro-optic polarization rotator. FIG. 6A shows scattered radiation 112 having radiation with polarization in the $\lambda 1$ direction. The scattered radiation 112 enters the half-wave plate 116 while a voltage is applied by a voltage source 150. The half-wave plate 116 allows the scattered radiation 112, polarized in the $\lambda 1$ direction, to pass without any change in the polarization. The scattered radiation 112, still polarized in the $\lambda 1$ direction, may then enter the detector 118 (FIG. 1A), where a spectrum can be measured. The half-wave plate 116 may then be adjusted to another position such that the half-wave plate 116 rotates the scattered radiation 112 passing therethrough. For example, and as shown in FIG. 6B, the voltage applied by the voltage source 150 may be reversed, which rotates the scattered radiation 112 passing therethrough by 90°. Thus, if the scattered radiation 112 is polarized in the $\lambda 2$ direction, the half-wave plate 116 may rotate the scattered radiation 112 to the $\lambda 1$ direction. The rotated scattered radiation 112 may enter the detector 118 (FIG. 1A), where a spectrum can be measured. The spectra may be measured using the same polarization even though the scattered radiation 112 leaves the test sample 106 at different polarizations $\lambda 1$ and $\lambda 2$. Though shown as an electro-optic polarization rotator, the half-wave plate 116 alternatively may be any selected half-wave plate, including a device configured to be mechanically rotated to achieve the effect shown in FIGS. 6A and 6B.

The spectrometer 100 may be used to acquire a spectrum based on the first beam 132a, followed by a spectrum based on the second beam 132b. Thus, the spectrometer 100 may be used to detect responses of the test sample 106 to two different wavelengths of radiation. Furthermore, the half-wave plate 116 may be used to obtain two different spectra at different polarizations from the same incident beam. Many Raman shifts vary based on the polarization at which the incident beam is measured. Fluorescence often is independent of polarization. Therefore, by comparing spectra obtained at different polarization, the fluorescence, which may be common to both, may be subtracted out. Thus, the use of the half-wave plate 116 may yield two spectra instead of one, and each spectrum may have less noise than it otherwise would without comparison to another spectrum. That is, polarization may assist in discriminating Raman responses from fluorescence.

In some embodiments, the spectrometer 100 may be used to excite Raman scattering of the test sample 106 at a first wavelength and a second wavelength along a common path because the first wavelength is polarized in a first direction λ1 and the second wavelength is polarized in a second direction λ2 perpendicular to the first direction λ1. The beam combiner 142 may be configured to combine beams linearly polarized in different directions with near 100% efficiency. Beam combiners (which are also known as "splitters" when used to separate beams of different polarizations) are described generally in U.S. Pat. No. 7,423,731, "Illumination Optical System, Exposure Apparatus, and Exposure Method with Polarized Switching Device," granted Sep. 9, 2008, the entire disclosure of which is incorporated herein by this reference.

The spectrometer 100 may collect a first Raman spectrum from the portion of scattered radiation 112 from the test sample 106 that is polarized in the first direction λ1 (i.e., radiation scattered from the first incident plane-polarized beam 104a). The spectrometer 100 may collect a second Raman spectrum from the portion of scattered radiation 112 from the test sample 106 that is polarized in the second direction λ2 (i.e., radiation scattered from the second incident plane-polarized beam 104b). The first Raman spectrum and the second Raman spectrum need not be collected simultaneously, and the incident plane-polarized beams 104a, 104b need not be delivered to the test sample 106 simultaneously. The first Raman spectrum and the second Raman spectrum may be compared or "decomposed" mathematically to produce a spectrum substantially free of fluorescence or background radiation.

Figure 7:
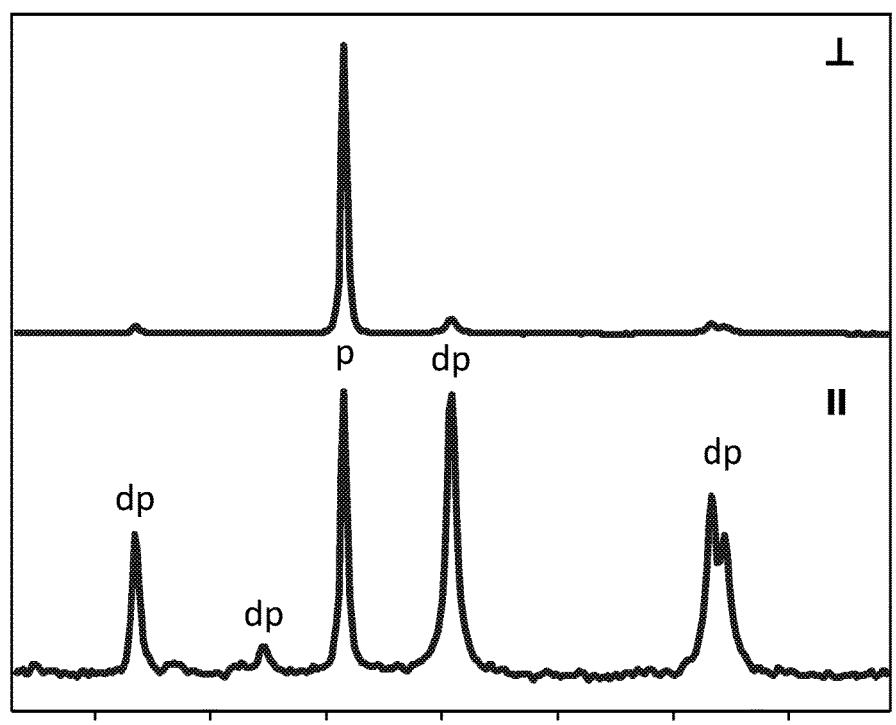
FIG. 7 shows Raman spectra collected from a sample of benzene at two orthogonal polarizations.

Materials exhibit different Raman spectra when excited by laser radiation having different polarization, even if the radiation is of the same wavelength. In some embodiments, the polarization states of both the first beam 132a and the second beam 132b may be changed, and Raman spectra may be collected from each of the polarization states generated by each of the first and second beams 132a, 132b. A decomposed Raman spectrum may be formed based on the spectra associated with each of the first and second beams 132a, 132b. FIG. 7 shows Raman spectra collected from a sample of benzene at two orthogonal polarizations at a wavelength of 785 nm. The top spectrum, collected from a sample excited with a perpendicular polarized beam, shows a strongly polarized Raman peak (p). Though most Raman peaks from benzene molecules are depolarized (dp), this one strongly polarized peak causes the Raman spectrum to be very different when the orthogonal polarization is used for excitation, as shown in the bottom spectrum. Differences in Raman spectra at different polarizations may be used to assist in identifying a material. For example, in addition to matching peak wavelengths at one polarization to a database of known spectra, peak wavelengths at another polarization may be compared to improve confidence in the match. Thus, the Raman spectra may be used to improve chemometric accuracy.

Figure 8:
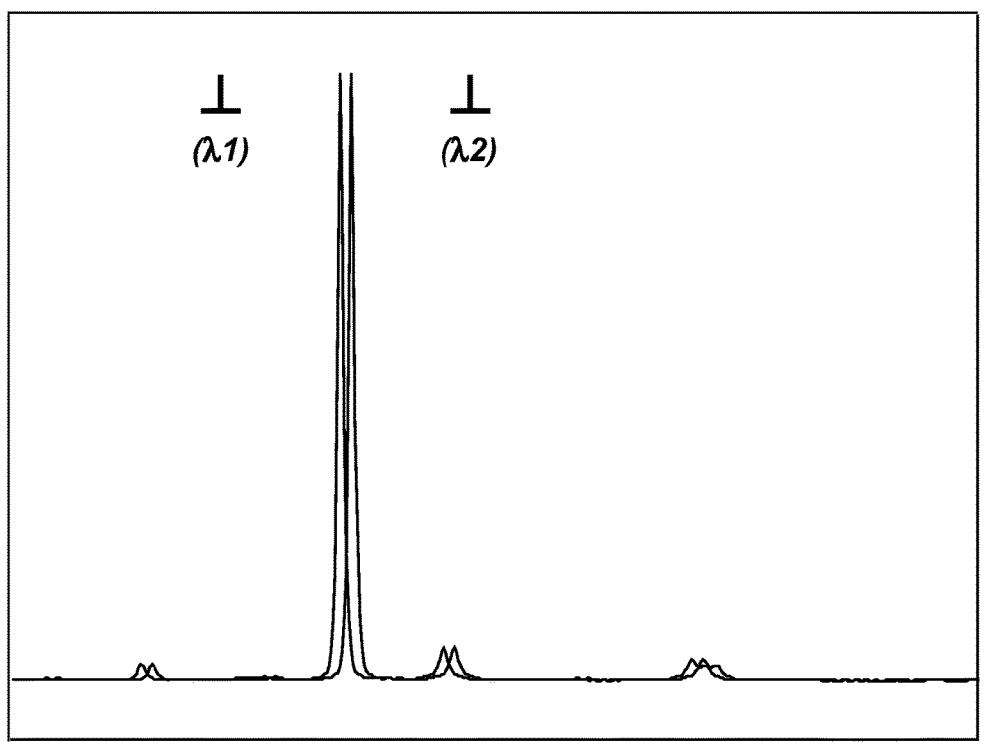
FIG. 8 shows Raman spectra collected from a sample of benzene at two different wavelengths.

The half-wave plate 116 (FIG. 1A), if present, may be beneficial to allow the spectrometer 100 to obtain spectra that are comparable by converting the scattered radiation to the same polarization. FIG. 8 shows Raman spectra λ1 and λ2 collected from a sample of benzene at two different wavelengths, 783 nm and 785 nm, respectively. The second spectrum λ2 was measured from scattered radiation that was rotated by a half-wave plate 116 to be in the same orientation as the scattered radiation from which the first spectrum λ1 was measured. Thus, as shown in FIG. 8, both spectra have peaks at similar wavenumbers and of similar intensities, with variations due to the small difference in the excitation wavelengths.

Figure 9A:
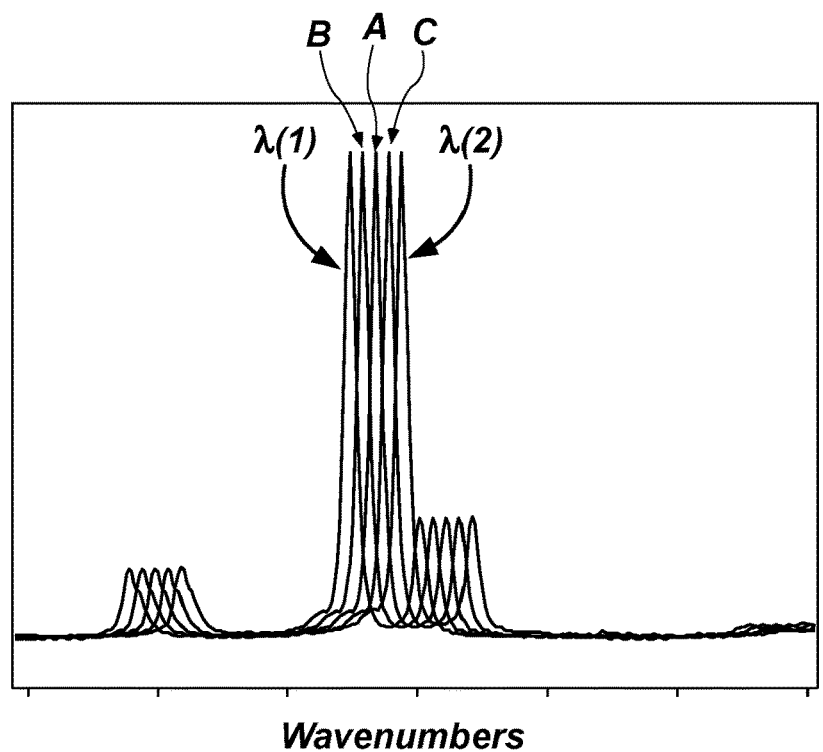
FIG. 9A shows measured and interpolated Raman spectra of a sample of benzene.
Figure 9B:
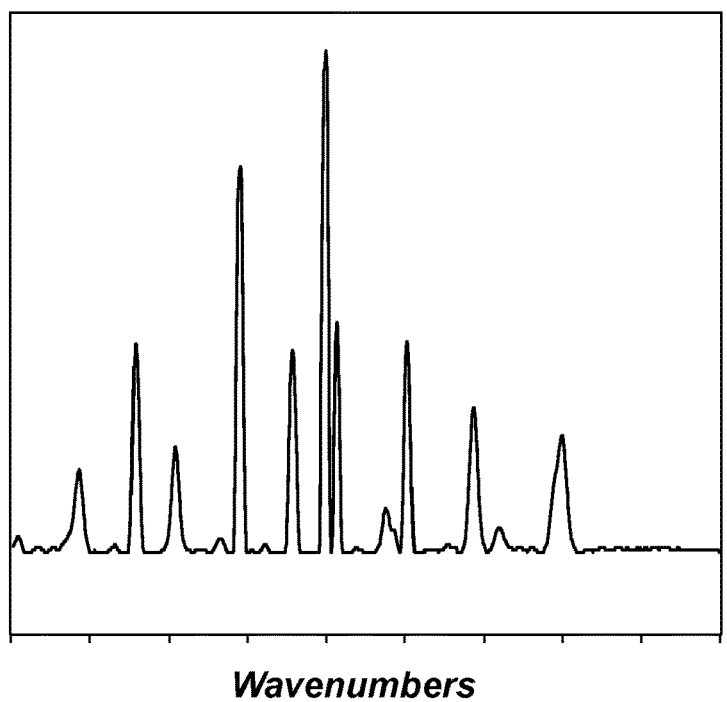
FIG. 9B shows a calculated spectrum substantially free of fluorescence and noise, based on the spectra of FIG. 9A.

Two Raman spectra measured using different excitation wavelengths can be used to interpolate one or more intermediate spectra between the two measured spectra (i.e., calculate a spectrum excited by a theoretical intermediate wavelength to the two wavelengths used to collect the two measured spectra). FIG. 9A shows two collected Raman spectra λ(1) and λ(2) measuring scattered radiation from the same sample excited at two different wavelengths. FIG. 9A also shows three interpolated spectra A, B, and C, between the collected Raman spectra λ(1) and λ(2). For example, spectrum A may be calculated by the average of λ(1) and λ(2): A=(λ(1)+λ(2))/2. Spectra B and C may be calculated by the average of A and λ(1), and A and λ(2), respectively: B=(λ(1)+A)/2; C=(A+λ(2))/2. The five spectra may be used to calculate a decomposed spectrum substantially free of noise (fluorescence and background radiation), as shown in FIG. 9B. Note that the horizontal axis is different between FIGS. 9A and 9B, and that FIG. 9B shows more of the decomposed spectrum. Mathematical calculations to generate such spectra are set forth in U.S. Pat. No. 8,570,507, "Method and Apparatus for Acquiring Raman Spectra without Background Interferences," issued Oct. 29, 2013, the entire disclosure of which is incorporated herein by this reference.

Figure 10:
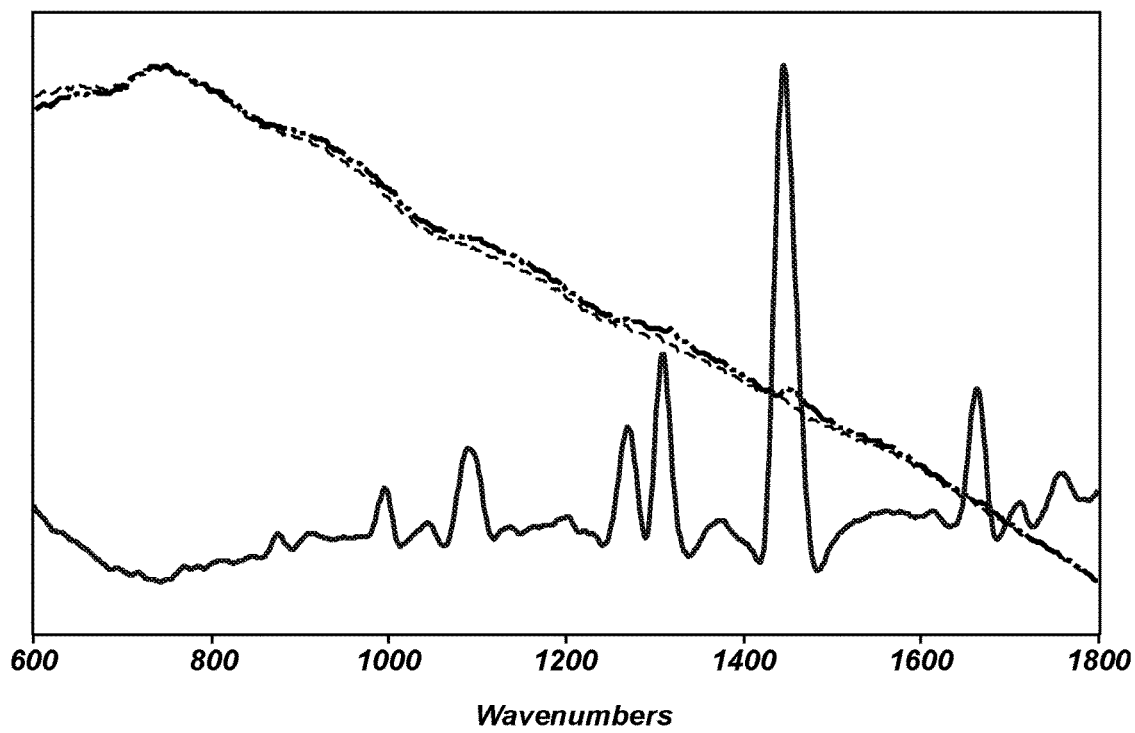
FIG. 10 shows Raman spectra measured from a sample of sesame oil excited by 783 nm and 785 nm lasers, as well as a decomposed spectrum substantially free of fluorescence.

A significant fraction of materials or material samples exhibit fluorescence, which tends to mask Raman signals of the materials. The fluorescence is typically independent of excitation wavelength, at least for small differences in excitation wavelength. When spectra are acquired at two slightly different wavelengths, the fluorescence in each spectrum should be approximately the same, though the Raman peaks should shift with excitation wavelength. Thus, the spectra can be decomposed (e.g., by principal component analysis or by subtraction of one spectrum from the other) to generate a spectrum free of fluorescence. FIG. 10 shows Raman spectra measured from a sample of sesame oil excited by 783 nm and 785 nm lasers. Because the sample is highly fluorescent, neither of these spectra has easily identifiable and quantifiable peaks. Thus, conventional Raman spectroscopy at either wavelength would not be effective to distinguish sesame oil from other materials.

However, when the two measured spectra are decomposed, as shown in FIG. 10, clear peaks appear. Thus, by measuring two Raman spectra from scattered radiation generated by slightly different excitation wavelengths, the effect of fluorescence of the spectra can be removed. Therefore, background decomposition methods disclosed herein can be used for samples that are not amenable to analysis by conventional Raman spectroscopy. The method may also be used to remove the effect of ambient background radiation, such as sunlight or room lighting.

Figure 11:
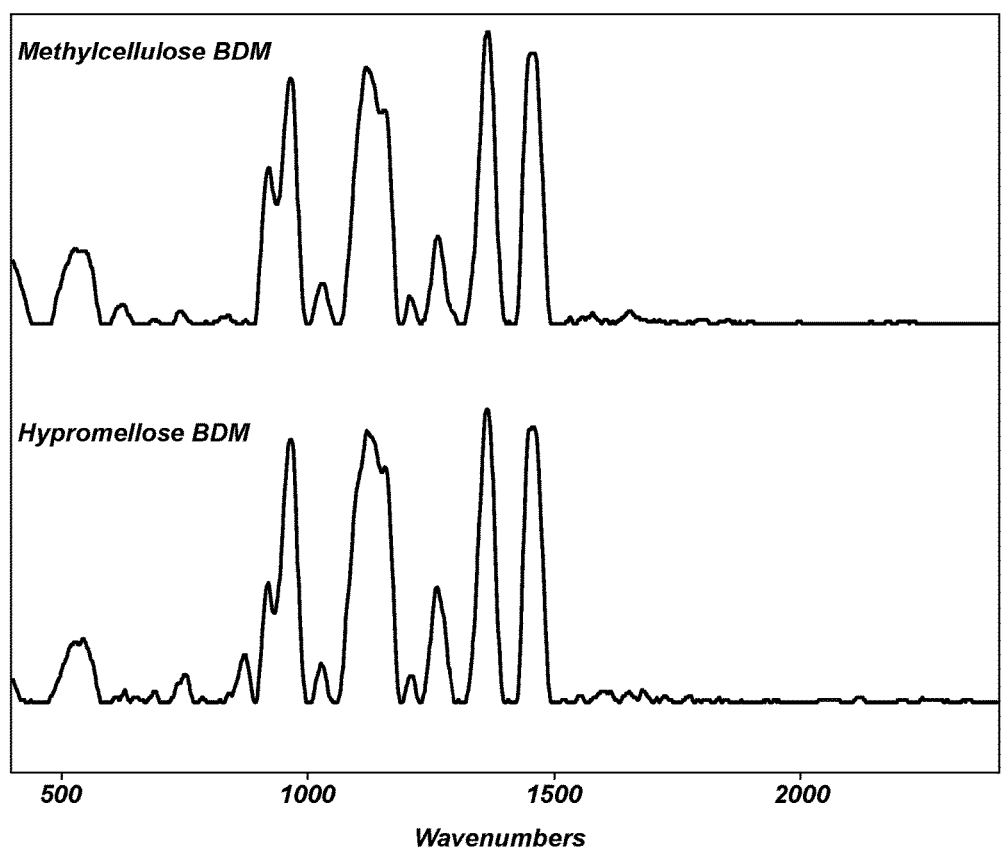
FIG. 11 shows decomposed spectra calculated from two Raman spectra of methylcellulose and hypromellose excited by 783 nm and 785 nm lasers.

As another example, FIG. 11 shows decomposed spectra from ethylcellulose and hypromellose (i.e., hydroxypropyl methylcellulose), materials that have similar chemical structures and that each exhibit high fluorescence. The spectra show identifiable, quantifiable peaks. Thus, the background decomposition methods disclosed herein can be used to identify and distinguish these two compounds.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the invention as hereinafter claimed, including legal equivalents thereof. In addition, features from one embodiment may be combined with features of another embodiment while still being encompassed within the scope of the invention as contemplated by the inventors. Further, embodiments of the disclosure have utility with different and various types and configurations of spectrometers.

What is claimed is:

1. A method of measuring Raman scattering from a sample, comprising:
    exciting Raman scattering of a sample with a first beam of electromagnetic radiation having a first wavelength traveling along an optical path to form a first scattered radiation, wherein the first beam is provided to the sample polarized in a first direction;
    exciting Raman scattering of the sample with a second beam of electromagnetic radiation having a second wavelength traveling along the optical path to form a second scattered radiation, wherein the second beam is provided to the sample polarized in a second direction perpendicular to the first direction;
    rotating, with a half-wave plate, one of the first beam or the second beam to have the same polarization direction as the other of the first beam or the second beam;
    collecting a first Raman spectrum from the first scattered radiation;
    collecting a second Raman spectrum from the second scattered radiation; and
    forming a decomposed Raman spectrum based on the first Raman spectrum and the second Raman spectrum.

2. The method of claim 1, wherein exciting Raman scattering of the sample with a second beam comprises exciting Raman scattering of the sample at a second wavelength different from the first wavelength and within 10 nm of the first wavelength.

3. The method of claim 1, wherein exciting Raman scattering of a sample with a first beam of electromagnetic radiation comprises maintaining a constant temperature of a first electromagnetic source configured to emit the first beam and wherein exciting Raman scattering of the sample with a second beam of electromagnetic radiation comprises maintaining a second electromagnetic source configured to emit the second beam at the constant temperature.

4. The method of claim 1, further comprising rotating, with a second half-wave plate, one of the first scattered radiation or the second scattered radiation to have the same polarization direction as the other of the first scattered radiation or the second scattered radiation.

5. The method of claim 1, wherein rotating, with a half-wave plate, one of the first beam or the second beam to have the same polarization direction as the other of the first beam or the second beam comprises passing the one of the first beam or the second beam through the half-wave plate.

6. The method of claim 5, wherein:
    collecting a first Raman spectrum from the first scattered radiation comprises passing the first scattered radiation through the half-wave plate in a first position; and
    collecting a second Raman spectrum from the second scattered radiation comprises passing the second scattered radiation through the half-wave plate in a second position.

7. The method of claim 5, wherein passing the one of the first beam or the second beam through the through a half-wave plate comprises passing the one of the first beam or the second beam through an electro-optic polarization rotator.

8. The method of claim 1, further comprising collecting at least a third Raman spectrum from the first scattered radiation or the second scattered radiation.

9. The method of claim 8, further comprising comparing the at least a third Raman spectrum with the first Raman spectrum or the second Raman spectrum to discriminate the Raman spectra from fluorescence.

10. The method of claim 8, wherein forming a decomposed Raman spectrum comprises forming a decomposed Raman spectrum based on the first Raman spectrum, the second Raman spectrum, and the at least the third Raman spectrum.

11. The method of claim 1, wherein forming a decomposed Raman spectrum comprises interpolating between the first Raman spectrum at the first wavelength and the second Raman spectrum at the second wavelength, the second wavelength different from the first wavelength.

12. The method of claim 1,
    wherein exciting Raman scattering of the sample with the first beam of electromagnetic radiation comprises:
    passing the first beam through a first polarizing device to form a first linear polarized beam; and
    passing the first linear polarized beam to a beam combiner;
    wherein exciting Raman scattering of the sample with the second beam of electromagnetic radiation comprises:
    passing the second beam through a second polarizing device to form a second linear polarized beam having a polarization orthogonal to a polarization of the first linear polarized beam; and
    passing the second linear polarized beam to the beam combiner.

13. The method of claim 1, further comprising changing a polarization of an excitation source that provides at least one of the first beam or the second beam of electromagnetic radiation, the second wavelength different from the first wavelength.

14. A spectrometer, comprising:
    a first electromagnetic source adapted to provide a first beam having a first wavelength;
    a first polarized device configured to convert the first beam to a first polarized beam polarized in a first direction;
    a second electromagnetic source adapted to provide a second beam having a second wavelength;
    a second polarized device configured to convert the second beam to a second polarized beam polarized in a second direction;
    a half-wave plate configured to rotate one of the first beam or the second beam to have the same polarization direction as the other of the first beam or the second beam while allowing the other of the first beam or the second beam to pass therethrough without changing the polarization thereof;
    a beam combiner configured to combine the first polarized beam and the second polarized beam to form orthogonal collinear polarized beams traveling along a common optical path and directed toward a test sample; and
    a detector adapted to receive scattered radiation from the test sample and detect a spectroscopy signal from the scattered radiation.

15. The spectrometer of claim 14, wherein the first wavelength is approximately 785 nm and the second wavelength is approximately 783 nm.

16. The spectrometer of claim 14, wherein the second wavelength is different from the first wavelength and a difference between the first wavelength and the second wavelength is less than 10 nm.

17. The spectrometer of claim 14, wherein a difference between the first wavelength and the second wavelength is approximately 2 nm.

18. The spectrometer of claim 14, wherein each of the first polarized device and the second polarized device comprises a quarter-wave plate.

19. The spectrometer of claim 14, further comprising at least one temperature regulator configured to maintain at least one of the first electromagnetic source and the second electromagnetic source at a constant temperature while the first electromagnetic source or the second electromagnetic source provides the first beam or the second beam.

20. The spectrometer of claim 19, wherein the at least one temperature regulator comprises a thermoelectric device.

21. The spectrometer of claim 14, further comprising a second half-wave plate configured to rotate scattered radiation from the test sample polarized in one of the first direction or the second direction while allowing the scattered radiation polarized in the other of the first direction or the second direction to pass therethrough without changing the polarization direction thereof.

22. The spectrometer of claim 14, wherein the half-wave plate comprises an electro-optic polarization rotator.

* * * * *